United States Patent [19]

Schöllermann et al.

[11] Patent Number: 6,151,107
[45] Date of Patent: Nov. 21, 2000

[54] METHOD OF NON-INVASIVE DETERMINATION OF OXYGEN SATURATION IN TISSUE IN WHICH BLOOD IS CIRCULATING

[75] Inventors: Hans Schöllermann, Grenzach-Wyhlen, Germany; Patrick Eberhard, Allschwil, Switzerland

[73] Assignee: Linde Medical Sensors AG, Basel, Switzerland

[21] Appl. No.: 09/214,978

[22] PCT Filed: Jul. 24, 1997

[86] PCT No.: PCT/CH97/00282

§ 371 Date: Jan. 15, 1999

§ 102(e) Date: Jan. 15, 1999

[87] PCT Pub. No.: WO98/04903

PCT Pub. Date: Feb. 5, 1998

[30] Foreign Application Priority Data

Jul. 26, 1996 [CH] Switzerland ............................. 1864/96

[51] Int. Cl.[7] .............................. G01N 33/48; A61B 5/00
[52] U.S. Cl. ................................. 356/41; 356/39; 356/42; 600/330
[58] Field of Search .................... 356/39, 40, 41, 356/42; 600/330

[56] References Cited

U.S. PATENT DOCUMENTS 5,216,598  6/1993  Branstetter et al. .

5,224,478  7/1993  Sakai et al. .............................. 356/41
5,278,627  1/1994  Aoyagi et al. .
5,497,769  3/1996  Gratton et al. ........................... 356/41

FOREIGN PATENT DOCUMENTS 0303502  2/1989  European Pat. Off. .
0335356  10/1989  European Pat. Off. .
4429758  2/1996  Germany .
9403102  2/1994  WIPO .

OTHER PUBLICATIONS

Schmitt, J.M., "Simple Photon Diffusion Analysis of the Effects of Multiple Scattering on Pulse Oximetry," IEEE Transactions on Biomedical Engineering, vol. 38, No. 12, Dec. 1991.

*Primary Examiner*—Frank G. Font
*Assistant Examiner*—Roy M. Punnoose
*Attorney, Agent, or Firm*—Selitto & Associates

[57] ABSTRACT

In a method for the non-invasive determination of the oxygen saturation in tissue supplied with blood, the tissue is irradiated with red and infrared light and the DC and AC components of the emerging light are measured. During a first time interval, a calibration factor k is determined from the DC and AC components of the emerging light. During a second time interval, the oxygen saturation in the tissue is computed progressively from the DC components of the emerging light and the determined calibration factor k.

10 Claims, 2 Drawing Sheets

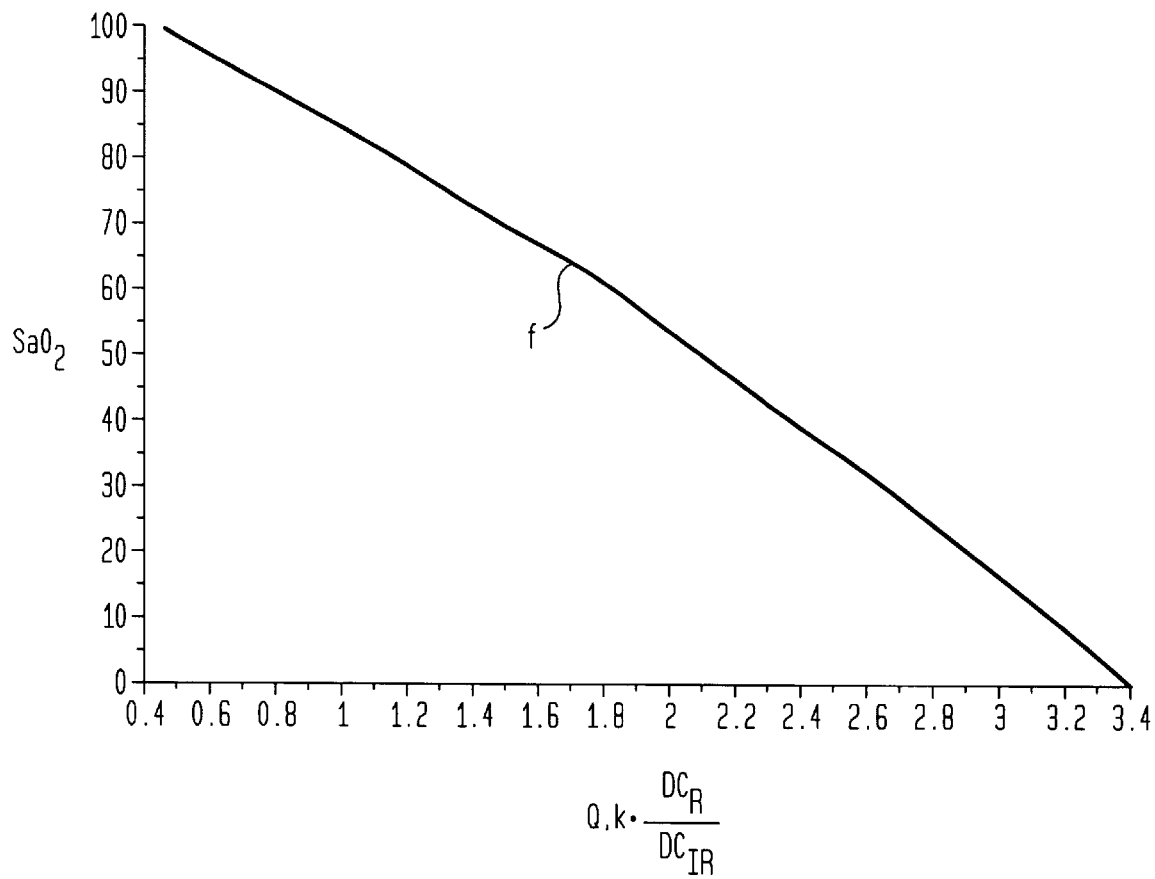

METHOD OF NON-INVASIVE DETERMINATION OF OXYGEN SATURATION IN TISSUE IN WHICH BLOOD IS CIRCULATING

FIELD OF THE INVENTION

The invention relates to a method for the non-invasive determination of the oxygen saturation in tissue supplied with blood.

BACKGROUND OF THE INVENTION

The optical measurement of the oxygen saturation of the haemoglobin in tissue supplied with blood has been known since 1932 and met with great interest at an early stage as a non-invasive method for the determination of the oxygen supply of living tissue in physiological research. Systems which were developed for the determination of this parameter originally made use of measurement methods which resembled spectrophotometric methods; in this case, the earlobe was frequently used as test object. In a similar way to a test cell, the earlobe was irradiated with light at different wavelengths. The oxygen saturation was computed from the measured intensities of the transmitted light. Principles of these computations were the known absorption spectra of haemoglobin in its form saturated with oxygen (oxyhaemoglobin, FIG. 1, spectrum 1) and its oxygen-free form (reduced haemoglobin, FIG. 1, spectrum 2). A difficulty in this method, which was designated as ear oxymetry, resided in the fact that, in contrast to a test cell, a precise calibration of the optical system was not possible and, accordingly, the measurement method remained relatively imprecise. It proved to be difficult to take adequate account of the influences of tissue thickness, blood content, light intensities and other variables. It was indeed inter alia attempted, by application of pressure to the tissue, temporarily to remove the blood contained therein and thereby to generate an artificial null point. However, experiments of this type proved to be impractical and too imprecise. In addition, use was made of the fact that the absorption coefficients of oxyhaemoglobin and reduced haemoglobin at a few wavelengths (e.g. 505 nm, 548 nm and 805 nm) have equal values (isoabsorption points 3, FIG. 1). By using one of these wavelengths, a reference point independent of the oxygen saturation was indeed established, but this reference point alone (without a second reference quantity) was not sufficient. Ear oxymetry was further refined in the sixties. Thus, in a system (HP 47201A ear oxymeter) developed by the company Hewlett Packard eight wavelengths were used, with the aid of which further reference points were used for the calibration of the measurement system. This method also proved to be very demanding and costly in implementation. Accordingly, ear oxymetry never gained access to clinical routine applications and was employed almost exclusively in physiological research and for specific experimental questions, e.g. aviation and other fields.

Not until the early eighties was a new method developed, which became known under the designation pulse oxymetry and which became well established within a short time as a routine method for monitoring patients, especially during anaesthesia and intensive care. The principle of pulse oxymetry is based on recording the changes in absorption in the test object, which changes are caused by the arterial blood flowing in in the form of pulses. This permits a measurement of the oxygen saturation of the haemoglobin in the arterial blood (arterial oxygen saturation). As shown in FIG. 2, the total absorption of light in tissue supplied with blood is composed of the following components:

Absorption 4 by tissue and bones

Absorption 5 by venous blood

Absorption 6 by arterial blood

Variable absorption 7 as a consequence of volume changes which are generated by the pulsating arterial blood.

The first three components are, as a rule, steady over a relatively long period of time and are combined hereinbelow as the DC component. Only the fourth component (AC component) is periodically time-dependent in synchronism with the heart contractions.

As a rule, two light emitting diodes (LEDs) having wavelengths of approximately 660 nm (red) and approximately 890 nm (infrared) are used as light sources in pulse oxymetry. As is evident from FIG. 1, the light absorption of haemoglobin at 660 nm is greatly dependent upon the oxygen content of the blood. In contrast, the infrared wavelength is located in the vicinity of the isoabsorption point 3 of 805 nm, so that only a slight dependence of the light absorption upon the oxygen content is present. Accordingly, the absorption in the infrared range is used as reference quantity. The light emitted by the two LEDs is passed into a body part having a good supply of blood (e.g. pad of the finger, earlobe or toe). The light is repeatedly scattered therein and partially absorbed. The emerging light is measured by means of a photodiode which, as a rule, is disposed opposite to the LEDs. The two LEDs and the photodiode are usually integrated in one component, which is designated as a pulse oxymetric sensor. The separate measurement of the red and infrared light using only one photodiode is made possible by the use of alternating light pulses of the two wavelengths, which are metrologically detected and evaluated separately.

SUMMARY OF THE INVENTION

For the pulse oxymetric determination of the arterial oxygen saturation ($SaO_2^P$), the steady components ($DC_R$, $DC_{IR}$) and the time-dependent components $AC_R$, $AC_{IR}$) of the measured red (R) and infrared (IR) Light intensities are utilized. Usually, $SaO_2^P$ is determined by means of the relation $$SaO_2^P = f(Q) \text{ where } Q = \frac{AC_R}{DC_R} : \frac{AC_{IR}}{DC_{IR}} \qquad (1)$$

where f represents an empirically determined function (see FIG. 3), which, for a predetermined measurement system (pulse oxymeter and sensor), is independent of measurement position and patient.

A problem which has not yet been satisfactorily solved in pulse oxymetric measurement resides in that disturbances of the measurement signals which are caused by movements of the patient or his environment cannot in many cases be fully eliminated. This is so in particular in circumstances in which during weak physiological signals very strong movement-conditioned disturbances occur. Thus, it may certainly happen that the ratio $AC_R/DC_R$ or $AC_{IR}/DC_{IR}$ is smaller than $10^{-3}$, while the disturbance signals conditioned by movements are a hundred times greater. Since the frequency distribution of movement artifacts in many cases overlaps that of the physiological signal, a clear separation of the measurement signals from the disturbance signals by filtering is not possible in such cases. The determination of $SaO_2$ in accordance with equation (1) is then no longer guaranteed with sufficient accuracy, so that considerable measurement errors may occur. As a rule, disturbances of this type are recognized by the software of the system, and the operator of the pulse oxymeter is notified, e.g. by means of a message appearing on the display of the system, that the measurement is no longer possible. The operator of the pulse oxymeter now has the opportunity to eliminate the cause of the disturbance; however, this is not always feasible. Movement disturbances during the monitoring of neonates are particularly problematic. In such cases, the pulse oxymetric sensor is in most instances fitted to the surface of the hand or to the foot of the patient. Maintaining the hand or the foot stationary is, as a rule, not possible. Added to this is the fact that, specifically at these sensor positions, the measurement signal is in many cases very weak. For these reasons, in the course of the monitoring of neonates there frequently arises the situation that during a relatively long period of time the measurement of the arterial oxygen saturation has to be suspended. This is critical specifically in the case of those born prematurely with immature lungs, since in the case of these patients rapid and unexpected changes in the arterial oxygen saturation may occur, which changes may lead to severe complications if they are not recognized.

The object of the invention is to permit the determination of the oxygen saturation in situations in which, by reason of simultaneously existing weak physiological signals and strong movement-conditioned disturbance signals, the pulse-oxymetric method can no longer be used.

This object is achieved by the method according to the invention.

DETAILED DESCRIPTION OF THE INVENTION

Figure 1:
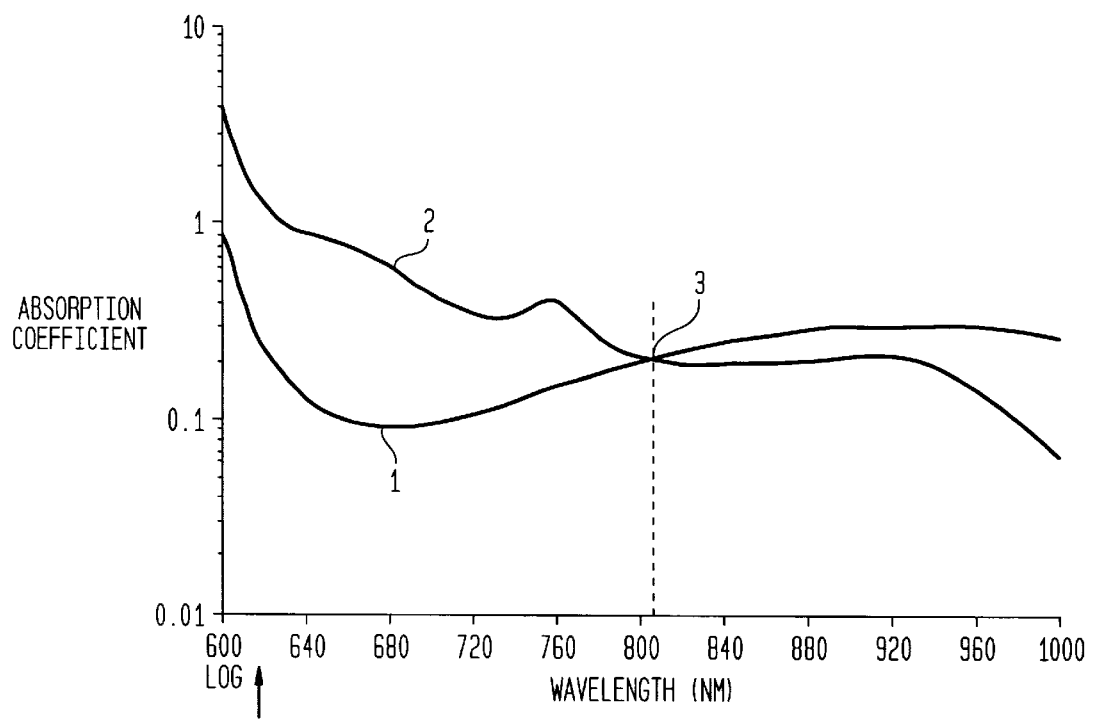
Figure 2:
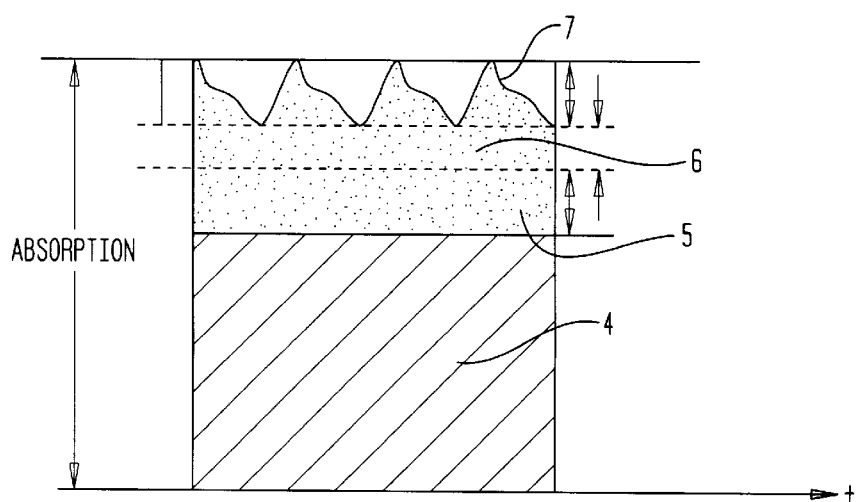

As predominantly steady quantities, the DC components of the red and infrared light emerging from the tissue are substantially less influenced by movement-conditioned disturbances than the quotients $AC_R/DC_R$ and $AC_{IR}/DC_{IR}$. Accordingly, it is recommended in the case of the above-described disturbance situations to use only the DC components for the computation of the oxygen saturation, as was carried out in the case of the initially described ear oxymetry. The fundamental difficulty of ear oxymetry resided as described above, in that a calibration of the measurement system was not possible, and that accordingly the influences of tissue thickness, blood content and other variables could not be taken into consideration with sufficient accuracy and by simple means.

With the method according to the invention, this problem is solved in that the pulse oxymetric measurement of the oxygen saturation ($SaO_2^P$) is used for the calibration of the oxygen saturation values ($SaO_2^{DC}$) determined by means of the DC components. The method is based on the observation that, to an approximation, the relation $$Q = k \cdot \frac{DC_R}{DC_{IR}} \quad (2)$$

is applicable between the quotient Q defined in equation (1) and the ratio $DC_R/DC_{IR}$, where the factor k remains unchanged, as long as the pulse oxymetric sensor is situated at the same measurement position and as long as no changes to the blood volume and other variable parameters at the location of the measurement take place. The calibration takes place in that the factor k is determined in accordance with equation (2) at an instant at which no or only small movement-conditioned disturbances are present. After this, the oxygen saturation $SaO_2^{DC}$ for a specified time can be determined from the DC values in accordance with $$SaO_2^{DC} = f\left(k \cdot \frac{DC_R}{DC_{IR}}\right). \quad (3)$$

In this expression, f is the same empirically determined function in accordance with equation (1), which is used for the computation of $SaO_2^P$.

It has proved to be expedient to adapt the calibration factor k progressively during the pulse oxymetric measurement and, in the event of disturbance situations, to use the last determined value of k for the computation of $SaO_2DC$. In practice, it has become evident that no substantial changes to k occur within a period of time of 5 to 10 minutes, provided that the sensor remains at the same measurement position and no rapid blood pressure changes take place. Thus, disturbance situations over periods of time of this order of magnitude can be bridged over with the aid of the method according to the invention. During the monitoring of neonates, these times are in most cases sufficient, since extensive movements of the hands or feet are, as a rule, interrupted by brief rest pauses, during which a new determination of k can be undertaken.

It is understood that in place of the approximation specified in equation (2) it is also possible to use other, refined relationships between Q and $DC_R/DC_{IR}$ in the sense of the method according to the invention for calibration, where this is desired in the interests of enhanced accuracy. By way of example, a polynomial of the form $$Q = \sum_{i=1}^{n} k_i \cdot \left(\frac{DC_R}{DC_{IR}}\right)^{i-1} \quad \text{where } n \geq 2 \quad (4)$$

would be suitable for this purpose. However, the calibration would in this case be substantially more demanding, since a plurality of pairs of values of Q and $DC_R/DC_{IR}$ (at least n) would then have to be used for the determination of $k_1, \ldots, k_n$.

What is claimed is:

1. A method for non-invasive determination of oxygen saturation in tissue supplied with blood, comprising the steps of:

irradiating the tissue with light of at least two different wavelengths;

measuring the DC components and the AC components of the light emerging from the tissue;

during a first time interval, determining at least one calibration factor from the DC and AC components of the emerging light; and during a second time interval, progressively computing the oxygen saturation in the tissue from the DC components of the emerging light and said at least one calibration factor.

2. The method according to claim 1, wherein the determining step includes determining said at least one calibration factor during the first time interval in which no movement-conditioned disturbances occur.—

3. The method according to claim 1, wherein the determining step includes determining said at least one calibration factor during the first time interval in which only small movement-conditioned disturbances occur.

4. The method according to claim 1, wherein the determining step is periodically repeated.

5. The method according to claim 4, wherein the determining step is repeated every 10 seconds to about 10 minutes.

6. The method according to claim 1, wherein the computing step includes using the equation $$SaO_2^{DC} = f\left(k \times \frac{DC_{L1}}{DC_{L2}}\right),$$

where $SaO_2^{DC}$ is the oxygen saturation, $DC_{L1}$ and $DC_{L2}$ are the DC components of the emerging light of the two wavelengths used, k is said at least one calibration factor, and f is an empirically determined function which, for a given measuring device, is independent of measurement position and patient.

7. The method according to claim 6, wherein said at least one calibration factor k is determined according to the equation $$k \times \frac{DC_{L1}}{DC_{L2}} = \frac{AC_{L1}}{DC_{L1}} : \frac{AC_{L2}}{DC_{L2}},$$

where $AC_{L1}$ and $AC_{L2}$ are the AC components of the emerging light of the two wavelengths used.

8. The method according to claim 1, wherein the computing step includes using the equation $$SaO_2^{DC} = f\left(\sum_{i=1}^{n} k_i \times \left(\frac{DC_{L1}}{DC_{L2}}\right)^{i-1}\right),$$

where $SaO_2^{DC}$ is the oxygen saturation,
$n \geq 2$, $DC_{L1}$ and $DC_{L2}$ are the DC components of the emerging light of the two wavelengths used, $k_1$ to $k_n$ are calibration factors, and f is an empirically determined function which, for a given measuring device, is independent of measurement position and patient.

9. The method according to claim 8, wherein said calibration factors $k_1$ to $k_n$ are determined according to the equation $$\sum_{i=1}^{n} k_i \times \left(\frac{DC_{L1}}{DC_{L2}}\right)^{i-1} = \frac{AC_{L1}}{DC_{L1}} : \frac{AC_{L2}}{DC_{L2}},$$

where $AC_{L1}$ and $AC_{L2}$ are the AC components of the emerging light of the two wavelengths used.

10. The method according to claim 1, wherein the irradiating step includes using red light and infrared light.

* * * * *